United States Patent [19]
Jung et al.

[11] Patent Number: 5,886,202
[45] Date of Patent: Mar. 23, 1999

[54] BRIDGED FLUORENYL/INDENYL METALLOCENES AND THE USE THEREOF

[76] Inventors: Michael Jung, Postfach 101251, D-95440 Bayreuth; Helmut G. Alt, Wacholderweg 27, D-95445 Bayreuth, both of Germany; M. Bruce Welch, 4750 Lewis Dr., Bartlesville, Okla. 74005

[21] Appl. No.: 928,820

[22] Filed: Sep. 12, 1997

Related U.S. Application Data

[63] Continuation-in-part of Ser. No. 779,496, Jan. 8, 1997, abandoned, and a continuation-in-part of Ser. No. 781,157, Jan. 8, 1997, abandoned, and a continuation-in-part of Ser. No. 779,497, Jan. 8, 1997, abandoned.

[51] Int. Cl.$^6$ ............................................. C07F 7/08
[52] U.S. Cl. .................... 556/11; 556/12; 556/43; 556/52; 556/53; 556/466; 556/489; 585/426; 526/92; 526/121; 526/122; 526/126; 526/127; 526/128
[58] Field of Search ................... 556/11, 12, 52, 556/53, 43, 466, 489; 585/426; 526/92, 121, 122, 126, 127, 128

[56] References Cited

U.S. PATENT DOCUMENTS

| | | | |
|---|---|---|---|
| 5,145,819 | 9/1992 | Winter et al. | 502/117 |
| 5,391,789 | 2/1995 | Rohrmann | 556/11 |
| 5,393,911 | 2/1995 | Patsidis et al. | 556/489 |
| 5,401,817 | 3/1995 | Palackal et al. | 526/127 |
| 5,436,305 | 7/1995 | Alt et al. | 526/160 |
| 5,498,581 | 3/1996 | Welch et al. | 502/102 |
| 5,539,066 | 7/1996 | Winter et al. | 5269/119 |
| 5,587,501 | 12/1996 | Winter et al. | 556/53 |
| 5,594,078 | 1/1997 | Welch et al. | 526/119 |
| 5,770,753 | 6/1998 | Kuber et al. | 556/11 |
| 5,780,659 | 7/1998 | Schmid et al. | 556/11 |
| 5,786,495 | 7/1998 | Resconi et al. | 556/11 |

FOREIGN PATENT DOCUMENTS

| | | | |
|---|---|---|---|
| 577581 | 1/1994 | European Pat. Off. | C08F 10/00 |
| 729978 | 9/1996 | European Pat. Off. | C08F 10/02 |

OTHER PUBLICATIONS

*Macromol. Symp.* 89, pp. 345–367 (1995), Razavi et al.

*Primary Examiner*—Paul F. Shaver
*Attorney, Agent, or Firm*—Edward L. Bowman

[57] ABSTRACT

Bridged fluorenyl/indenyl metallocenes having substituents at the 3 position of the indenyl and the use thereof in the polymerization of olefins are disclosed. Also a new method for preparing bridged fluorenyl/indenyl ligands wherein the indenyl has a substituent in the 3 position and the preparation of metallocenes with such ligands.

36 Claims, No Drawings

BRIDGED FLUORENYL/INDENYL METALLOCENES AND THE USE THEREOF

This application is a continuation-in-part of U.S. patent application Ser. No. 779,496, now abandoned; Ser. No. 779,497 now abandoned; and Ser. No. 781,157, now abandoned which were all filed Jan. 8, 1997. The disclosures of those copending applications are incorporated herein by reference.

FIELD OF THE INVENTION

The present invention relates to metallocenes. In a more specific aspect the invention relates to particular types of bridged fluorenyl/indenyl metallocenes having unusual effectiveness as catalysts for the polymerization of olefins. In another aspect the invention relates to the use of such metallocenes in the polymerization of olefins. Still another aspect of the invention relates to a method for preparing bridged fluorenyl/indenyl ligands having certain substituents at the 3 position of the indenyl, which ligands can be used to prepare the metallocenes of the present invention.

BACKGROUND OF THE INVENTION

Metallocenes are unique in the field of olefin polymerization in that it has been discovered that by changing the substituents on the organic ligands of the metallocene it is often possible to change certain effects that the metallocenes have on the polymerization process. Examples of changes observed following some changes of substituents include polymerization activity, polymer molecular weight, and comonomer selectivity. The process of determining what effect changes in substituents will have is, however, still largely empirical.

An object of the present invention is to provide certain bridged fluorenyl indenyl metallocenes that have improved properties as olefin polymerization catalysts.

Other aspects, objects, and advantages of the present invention will be apparent from the following disclosure.

SUMMARY OF THE INVENTION

The present invention is concerned with bridged fluorenyl/indenyl metallocenes of the formula

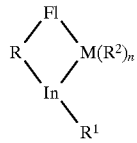

wherein R is a divalent organo radical connecting Fl and In, Fl is a 9-fluorenyl radical, In is an indenyl radical connected to R at the 1 position and to $R^1$ at the 3 position, wherein R and $R^1$ are the only substituents on In, wherein $R^1$ is selected from the group consisting of alkyl, aralkyl, alkenyl, alkylsilyl, alkenylsilyl, and alkoxyalkyl radicals having 1 to 20 carbon atoms, M is a metal selected from the group consisting of titanium, zirconium, hafnium, niobium, and tantalum, and each $R^2$ can be the same or different and is selected from hydrogen, halides, alkyl radicals containing 1 to 10 carbon atoms, aryl radicals having 6 to 12 carbon atoms, alkenyl radicals having 2 to 10 carbon atoms, arylalkyl radicals having 7 to 40 carbon atoms, arylalkenyl radicals having 8 to 40 carbon atoms, and alkylaryl radicals having 7 to 40 carbon atoms, n is a number to fill the remaining valences of M, further characterized by the fact that $R^1$ is not allyl if R is dimethylsilyl.

Another aspect of the invention relates to a method for preparing bridged fluorenyl/indenyl ligands having certain substituents at the 3 position of the indenyl, which ligands can be used to prepare the metallocenes of the present invention. Also in accordance with the present invention there is provided the process of using such metallocenes in the polymerization of olefins.

DETAILED DESCRIPTION OF THE INVENTION

The bridge R of the metallocenes of the present invention can be selected from any suitable divalent organo radicals, preferably those containing 1 to 20 carbon atoms. Some typical examples include dimethyl silyl, diphenyl silyl, phenyl methyl silyl, dimethyl methylene, 1-methyl-1-phenyl methylene, diphenylmethylene, alkenyl substituted ethylenes having 4 to 12 carbon atoms, alkyl substituted ethylenes having 4 to 12 carbon atoms, and unsubstituted ethylene, i.e. 1,2-ethylene. It is currently preferred that the fluorenyl radical be unsubstituted. The term methylene and ethylene as used herein are also sometimes referred to as methylidene and ethylidene, respectively.

Most of the metallocenes of the present invention can be produced by preparing the necessary organic ligand and then reacting the dilithium salt of the ligand with a suitable metal compound using techniques known in the art. Various techniques can be used to prepare the necessary organic ligand. One inventive technique involves reacting lithium fluorenyl with a benzofulvene in diethylether to produce a bridged fluorenyl/indenyl ligand lithium salt which is then reacted with an alkyl, alkenyl, or organosilyl halide to result in a bridged fluorenyl/indenyl ligand having the corresponding alkyl, alkenyl, or organosilyl halide in the 3 position on the indenyl.

After the reaction of the ligand salt with the metal compound the metallocene can be recovered and purified using conventional techniques known in the art such as filtration, extraction, crystallization, and recrystallization. It is generally desirable to recover the metallocene in a form that is free of any substantial amount of by-product impurities. Accordingly, recrystallization and fractional crystallization to obtain relatively pure metallocenes is desirable. Dichloromethane has been found to be particularly useful for such recrystallizations. Since the stability of the various metallocenes varies, it is generally desirable to use the metallocenes soon after their preparation or at least to store the metallocene under conditions favoring their stability. For example the metallocenes can generally be stored in the dark at low temperature, i.e. below 0° C., in the absence of oxygen and water.

The resulting inventive indenyl-containing metallocenes can be used in combination with a suitable cocatalyst for the polymerization of olefinic monomers. In such processes the metallocene or the cocatalyst can be employed on a solid insoluble particulate support. In a preferred process when the metallocene has a polymerizable group the metallocene is prepolymerized in the presence of the cocatalyst using the technique taught in U.S. Pat. No. 5,498,581. Preferably the prepolymerization is conducted in the presence of a particulate diluent such as silica or polyethylene.

Examples of suitable cocatalysts include generally any of those cocatalysts which have in the past been employed in conjunction with transition metal containing metallocene olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, triisobutyl aluminum, diethyl aluminum chloride, diethyl aluminum hydride, and the like.

The currently most preferred cocatalyst is an aluminoxane. Such compounds include those compounds having repeating units of the formula

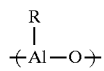

where R is an alkyl group generally having 1 to 5 carbon atoms.

Aluminoxanes, also sometimes referred to as poly (hydrocarbyl aluminum oxides) are well known in the art and are generally prepared by reacting an organo hydrocarbylaluminum compound with water. The currently preferred cocatalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096.

The indenyl-containing metallocenes in combination with the aluminoxane cocatalyst can be used to polymerize olefins, especially alpha olefins having 2 to 12 carbon atoms. Often such polymerizations would be carried out in a homogeneous system in which the catalyst and cocatalyst were soluble; however, it is within the scope of the present invention to carry out the polymerizations in the presence of supported or insoluble particulate forms of the catalyst and/or cocatalyst. The catalyst is thus considered suitable for solution, slurry, or gas phase polymerization. It is within the scope of the invention to use a mixture of two or more of the inventive indenyl-containing metallocenes or a mixture of an inventive indenyl-containing metallocene with one or more other cyclopentadienyl-type metallocenes.

The indenyl-containing metallocenes when used with aluminoxane are particularly useful for the polymerization of ethylene in the presence or absence of other olefins. Examples of other olefins that might be present include mono-unsaturated aliphatic alpha-olefins having 3 to 10 carbon atoms. Examples of such olefins include propylene, butene-1, pentene-1, 3-methylbutene-1, hexene-1, 4-methylpentene-1, 3-methylpentene-1, heptene-1, octene-1, decene-1, 4,4-dimethyl-1-pentene, 4,4-diethyl-1-hexene, 3-4-dimethyl-1-hexene, and the like and mixtures thereof.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914. It is considered that generally any of the polymerization procedures used in the prior art with any transition metal based catalyst systems can be employed with the present inventive indenyl-containing metallocenes.

The amount of cocatalyst can vary over a wide range. It is currently preferred for the molar ratio of the aluminum in the aluminoxane to the transition metal in the metallocene to be in the range of about 0.1:1 to about 100,000:1 and more preferably about 5:1 to about 15,000:1. In many cases, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about −60° C. to about 300° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

A further understanding of the present invention and its objects and advantages will follow from the following examples.

EXAMPLE 1

Synthesis of Omega Alkenyl Silyl Indene and other Indenes

Dimethyl chlorosilane was reacted with an excess 1,5-hexadiene in the presence of a platinum catalyst to form dimethyl-5-hexenylchloro silane. Then indene was reacted with butyl lithium in a mixture of diethyl ether and tetrahydrofuran to produce the indenyl lithium salt which was then reacted with the dimethyl-5-hexenylchlorosilane to yield the omega alkenyl dimethyl indene which can be called 5-hexenyl-dimethyl-silyl-1-indene.

Other substituted indenes were prepared by substituting other organohalides for the above dimethylindenyl-5-hexenylchloro silane. The substituted indenes prepared included allyl-1-indene, 3-butenyl-1-indene, 4-pentenyl-1-indene, 5-hexenyl-1-indene, butyl-1-indene, hexyl-1-indene, and benzyl-1-indene.

EXAMPLE 2

Synthesis of Dihydrocarbyl Silyl Bridged Fluorenyl Indenyl Ligands

An unsubstituted indenyl or one of the 1-substituted indene compounds prepared in Example 1 were employed to produce silyl bridged ligands having fluorenyl and indenyl groups. This was done by reacting the respective indenyl with butyl lithium in diethyl either to form the corresponding indenyl lithium compound. A dihydrocarbyl dichlorosilane was reacted with fluorenyl lithium in pentane to produce the corresponding 9-fluorenyl dihydrocarbyl chlorosilane. Then the 9-fluorenyl dihydrocarbyl chlorosilane was combined with the indenyl lithium compound and stirred overnight. The mixture was hydrolyzed and dried over sodium sulfate and the organic phase dried using a vacuum. For purification the organic product was dissolved in pentane and filtered over silica gel. This general process produced the following ligands:

9-fluorenyl-1-indenyl dimethyl silane
9-fluorenyl-1-(3-allyl)indenyldimethylsilane
9-fluorenyl-1-(3-but-3-enyl)indenyldimethylsilane
9-fluorenyl-1-(3-pent-4-enyl)indenyldimethylsilane
9-fluorenyl-1-(3-hex-5-enyl)indenyldimethylsilane
9-fluorenyl-1-(3-hex-5-enyl-dimethyl-silyl) indenyldimethylsilane
9-fluorenyl-1-(3-benzyl)indenyldimethylsilane
9-fluorenyl-1-(3-butyl)indenyldimethylsilane
9-fluorenyl-1-(3-hexyl)indenyldimethylsilane

EXAMPLE 3

Preparation of Substituted Benzofulyenes 6,6-dimethyl Benzofulyenes was prepared by dissolving 0.14 mmol of indene with 0.17 mmol of dimethylketone in 60 ml of methanol and 0.17 mmol of pyrrolidine. The reaction mixture was stirred over night and then reacted with 11.5 ml (0.2 mol) glacial acetic acid and extracted by shaking with water and pentane. The organic phase was dried under a vacuum and distilled under high vacuum to yield 6,6-dimethyl-Benzofulyenes. A similar technique was used to prepare 6-methyl-6(3-butenyl)-Benzofulyenes using the methyl-(3-butenyl) ketone.

In another process 0.14 mol of sodium dust was added to 60 ml of ethanol. Then 0.14 mol of methyl phenyl ketone was added. Then 0.28 mol of indene was added dropwise and the mixture stirred for 15 hours under reflux. The resulting product was then diluted with water and extracted with pentane, the organic phase evaporated, the excess indene removed using HV distillation and the residue dissolved in pentane and filtered over silica gel to produce 6-methyl-6-phenyl-Benzofulyenes. A similar process was used to produce 6,6-diphenylbenzofulvene.

EXAMPLE 4

Preparation of $C_1$ Bridged Ligands

First 36 mmol of fluorene was dissolved in 100 ml of diethylether and slowly mixed with 36 mmol of n-butyl lithium provided via a 1.6M hexane solution at room temperature. The reaction mixture was stirred for several hours. Then an equimolar amount of a substituted Benzofulyenes was added and the mixture stirred overnight. Then the mixture was hydrolyzed with 50 ml of water, the organic phase dried over sodium sulfate and the solvent evaporated under vacuum. The residue was dissolved in pentane, the solution filtered over silica gel and crystallized at −18° C. This process produced the following ligands:
2-(9-fluorenyl)-2-(1-indenyl)propane
1-(9-fluorenyl)-1-(1-indenyl)-1-phenylethane
5-(9-fluorenyl)-5-(1-indenyl)-1-hexene In another process 36 mmol of fluorene was dissolved in 100 ml of diethylether and mixed with 36 mmol n-butyl lithium provided via a 1.6M hexane solution and then stirred for several hours. An equimolar amount of a Benzofulyenes is added and the mixture stirred over night. Then the mixture was cooled down to −78° C. and 36 mmol of a hydrocarbyl halide such as an alkyl, alkenyl, or organo silyl halide was added and the mixture stirred for 15 hours at room temperature. The reaction mixture was then hydrolyzed with 50 ml of water and the organic phase dried over sodium sulfate and the solvent evaporated under vacuum. For purification the residue was dissolved in pentane, the solution filtered over silica gel and crystallized at 18° C. This technique was used to prepare the following ligands:
2-(9-Fluorenyl)-2-[1-(3-allyl)-indenyl]propane
2-(9-Fluorenyl)-2-{1-[3-(3-butenyl)]-indenyl}propane
2-(9-Fluorenyl)-2-{1-[3-(4-pentenyl)]-indenyl}propane
2-(9-Fluorenyl)-2-{1-[3-(5-hexenyl)]-indenyl}propane
2-(9-Fluorenyl)-2-[1-(3-trimethylsilyl)-indenyl]propane
2-(9-Fluorenyl)-2-[1-(3-allyldimethylsilyl)-indenyl]propane
2-(9-Fluorenyl)-2-{1-[3-(5-hexenyldimethylsilyl)]-indenyl}propane
2-(9-Fluorenyl)-2-[10(3-butyl)-indenyl]propane
2-(9-Fluorenyl)-2-[1-(3-hexyl)-indenyl]propane
2-(9-Fluorenyl)-2-{1-[3-(2-methoxyethyl)]-indenyl }propane
2-(9-Fluorenyl)-2-[1-(3-methyldiphenylsilyl)-indenyl]propane
2-(9-Fluorenyl)-2-[1-(3-benzyl)-indenyl]propane
2-(9-Fluorenyl)-2-{1-[3-(2-phenyl-ethyl)]-indenyl}propane
1-(9-Fluorenyl)-1-[1-(3-allyl)-indenyl]-1-phenylethane
1-(9-Fluorenyl)-1-{1-[3-(3-butenyl)]-indenyl}-1-phenylethane
1-(9-Fluorenyl)-1-{1-[3-(4-pentenyl)]-indenyl}-1-phenylethane and isomer
1-(9-Fluorenyl)-1-{1-[3-(5-hexenyl)]-indenyl}-1-phenylethane and isomer
1-(9-Fluorenyl)-1-[1-(3-butyl-indenyl]-1-phenylethane and isomer
1-(9-Fluorenyl)-1-[1-(3-hexyl)-indenyl]-1-phenylethane and isomer
1-(9-Fluorenyl)-1-[1-(3-benzyl)-indenyl]-1-phenylethane and isomer
1-(9-Fluorenyl)-1-{1-[3-(2-phenyl-ethyl)]-indenyl}-1-phenylethane and isomer
1-(9-Fluorenyl)-1-[1-(3-trimethylsilyl)-indenyl]-1-phenylethane and isomer
1-(9-Fluorenyl)-1-[1-(3-allyldimethylsilyl)-indenyl]-1-phenylethane and isomer
1-(9-Fluorenyl)-1-{1-{3-(2-methoxyethyl)]-indenyl}-1-phenylethane and isomer
5-(9-Fluorenyl)-5-[1-(3-trimethylsilyl)-indenyl]-1-hexene and isomer
5-(9-Fluorenyl)-5-{1-[3-(3-butenyl)]-indenyl}-1-hexene and isomer

EXAMPLE 5

Preparation of Ethylidene Bridged Ligands

A series of ethylene bridged indenyl/fluorenyl ligands having omega alkene branches off the ethylene bridge were prepared by reacting various 1,2-epoxyalkenes with fluorenyl lithium to obtain the corresponding 1-fluorenyl-omega-alkenyl-2-ol. Then mesyl chloride, i.e., methane sulfonyl chloride, was added to that compound in the presence of trimethylamine and methylene chloride to produce the corresponding 1-fluorenyl-omega-alkenyl-2-mesylate. The mesylate was then reacted with indenyl lithium in diethyl ether and then hydrolyzed with water to produce the ligand. This process was used to produce the following ligands:
6-(9-fluorenyl)-5-(1-indenyl)-1-hexene
8-(9-fluorenyl)-7-(1-indenyl)-1-octene
10-(9-fluorenyl)-9-(1-indenyl)-1-decene Inventive fluorenyl/indenyl ethylene bridged ligands with substituents on the 3 position of the indenyl were prepared by reacting the substituted indenyl lithium compound with 1-bromo-2-(9-fluorenyl) ethane, hydrolyzing, and recovering and purifying. This process was used to produce the following ligands:
1-(9-fluorenyl)-2-(1-(3-allyl)indenyl)ethane
1-(9-fluorenyl)-2-(1-(3-but-3-enyl)indenyl)ethane
1-(9-fluorenyl)-2-(1-(3-pent-4-enyl)indenyl)ethane
1-(9-fluorenyl)-2-(1-(3-hex-5-enyl)indenyl)ethane
1-(9-fluorenyl)-2-(1-(3-hex-5-enyldimethylsilyl)indenyl)ethane
1-(9-fluorenyl)-2-(1-(3-benzyl)indenyl)ethane

EXAMPLE 6

Preparation of Metallocenes

The ligands of Examples 2, 4, and 5 were used to prepare metallocenes of zirconium and/or hafnium. The general process used involved dissolving 3 mmol of the ligand in 40 ml of diethylether and combining that with two equivalents of n-butyllithium provided via a 1.6M hexane solution and stirring for at least about eight hours at room temperature. Then one equivalent of zirconium tetrachloride or hafnium tetrachloride was added and the mixture stirred overnight.

Further processing was conducted according to the solubility of the product: for soluble complexes, the mixture is filtered directly from the thus produced lithium chloride; for less soluble complexes, either the solvent is evaporated and the residue extracted withe methylene chloride, or the complex was filtered over sodium sulfate and the product extracted with methylene chloride or toluene from the first and then the solvent was evaporated under vacuum.

Such a technique was also used to produce a metallocene using niobium pentachloride. The metallocene produced can be named 2-(9-fluorenylidene)-2-(1-(3-(3-butenyl) indenylidene) propane niobium trichloride.

EXAMPLE 7

Ethylene Polymerizations

Various zirconium containing metallocenes were then evaluated to compare their effectiveness in the polymerization of ethylene. The polymerizations were conducted in a laboratory autoclave with 1 liter reaction volume. For each polymerization the autoclave was filled with 500 ml of pentane 10 and 7 ml of methylaluminoxane. A catalyst solution was prepared by combining the respective metallocene with methylaluminoxane and toluene to produce a solution containing about 0.2 to about 0.5 mg of the metallocene per ml of toluene. Generally approximately 1 mg of the metallocene was employed in each polymerization.

In some case smaller amounts of metallocene were employed when it was recognized that the catalyst was extremely active. The autoclave was thermostated at 60° C. and ethylene was added to maintain a pressure of 10 bar while the reactor contents were stirred. The polymerization was terminated by venting the reactor. The reaction time was generally about 1 hour but varied for some runs because of the difference in activities of the catalysts.

A summary of the results obtained is provided by the following tables wherein ligands having similar bridging groups are grouped together in separate tables. In the tables the polymerizations were for 1 hour unless indicated otherwise. The molecular weight of the polymers was compared using intrinsic viscosity ($M_n$) which was determined in cis/trans decal using an Ubbelohde precision capillary viscometer at 135+/−0.1 ° C. Prior to the measurement, the polymer samples were weighed in sealable small flasks and dissolved in an exactly measured amount of decalin at 140°–150° C. over a period of three to four hours. Insoluble components were separated using hot filtration over glass wool. The intrinsic viscosity values were determined using available calibration curves.

TABLE 1

Dimethyl Methylene Bridged

| $R^1$ | Activity | $M_n$ | $M_p$ |
|---|---|---|---|
| H | 4200 | 100,000 | 135 |
| Me$_3$Si- | 16670 | 265,000 | 137 |
| (allyl)Me$_2$Si- | 19200 | 375,00 | 135 |
| allyl | 6300 | 240,000 | 133 |
| 1-butenyl | 10200 | 300,000 | 133 |
| 1-pentenyl | 17100 | 375,000 | 131 |
| 1-hexenyl | 30900 | 340,000 | 137 |
| butyl | 35500 | 340,000 | 141 |
| hexyl | 24100 | 340,000 | 139 |
| benzyl | 14200 | 320,000 | 138 |

TABLE 1-continued

Dimethyl Methylene Bridged

| $R^1$ | Activity | $M_n$ | $M_p$ |
|---|---|---|---|
| 2-phenylethyl | 25000 | 335,000 | 135 |
| 2-methoxyethyl | n.d. | 210,000 | 132 |

TABLE 2

Phenyl Methyl Methylene Bridged

| $R^1$ | Activity | $M_n$ | $M_p$ |
|---|---|---|---|
| H | 10400 | 185,000 | 134 |
| Me$_3$Si- | 53700 | 720,000 | 138 |
| (allyl)Me$_2$Si- | 11000$^f$ | 800,000 | 137 |
| allyl | 6200 | 580,000 | 134 |
| 1-butenyl | 8800$^g$ | 750,000 | 136 |
| 1-pentenyl | 16600$^d$ | 850,000 | 135 |
| 1-hexenyl | 6900$^h$ | 770,000 | 136 |
| butyl | 21600 | 620,000 | 138 |
| hexyl | 14500 | 620,000 | 139 |
| benzyl | 70000 | 680,000 | 133 |
| 2-phenylethyl | 34100$^j$ | 500,000 | 134 |

$^d$based on 120 minutes
$^f$based on 25 minutes
$^g$based on 140 minutes
$^h$based on 90 minutes
$^j$based on 20 minutes

TABLE 3

1-Methyl-2-(1-Butenyl)Methylene Bridged

| $R^1$ | Activity | $M_n$ | $M_p$ |
|---|---|---|---|
| H | 4400 | 210,000 | 133 |
| Me$_3$Si- | 23822 | 300,000 | 137 |
| 1-butenyl | n.d. | 410,000 | 137 |

TABLE 4

Dimethyl Silyl Bridged

| $R^1$ | Activity | $M_n$ | $M_p$ |
|---|---|---|---|
| H | 8700 | 310,000 | n.d. |
| allyl | 38200 | 350,000 | 134 |
| 1-butenyl | 57000 | 330,000 | 137 |
| 1-pentenyl | 90000 | 380,000 | 141 |
| 1-hexenyl | 26100 | 385,000 | 138 |
| 1-hexenyl Me$_2$Si- | 46000 | 380,000 | 138 |
| butyl | 33300 | 400,000 | 140 |
| hexyl | 39200$^k$ | 420,000 | 140 |
| benzyl | 138300$^l$ | 24,000 | 137 |

$^k$based on 45 minutes of polymerization
$^l$based on 15 minutes of polymerization

TABLE 5

Phenyl Methyl Silyl Bridged

| $R^1$ | Activity | $M_n$ | $M_p$ |
|---|---|---|---|
| allyl | 44,400 | 400,000 | 141 |
| 1-hexenyl | 43100 | 275,000 | 138 |

TABLE 6

Diphenyl Silyl Bridged

| R¹ | Activity | $M_n$ | $M_p$ |
|---|---|---|---|
| H | 21800 | 255,000 | 139 |
| allyl | 26500 | 410,000 | 131 |
| 1-butenyl | 54700[m] | 44,500 | 140 |
| 1-pentenyl | 82800[j] | 430,000 | 141 |
| 1-hexenyl | 53500 | 480,000 | 135 |
| 1-hexenyl)Me₂Si- | 45800 | 420,000 | 137 |

[m]based on 40 minutes of polymerization
[j]based on 30 minutes of polymerization

TABLE 7

Control Examples-Unsubstituted Indenyl Ethylene Bridge, Fluorenyl and Branch Bonded at 1-position on Bridge

| Branch | Activity | $M_n$ | $M_p$ |
|---|---|---|---|
| 1-butenyl | 11500 | 330,000 | 135 |
| 1-hexenyl | 9300 | 270,000 | 132 |
| 1-octenyl | 17300 | 270,000 | 136 |

TABLE 8

Ethylene Bridged

| R¹ | Activity | $M_n$ | $M_p$ |
|---|---|---|---|
| benzyl | 110000[l] | 140,000 | 139 |
| allyl | 153000 | 160,000 | 134 |
| 1-butenyl | 198000[n] | 125,000 | 135 |
| 1-pentenyl | 204000[n] | 180,000 | 140 |
| 1-hexenyl | 19800[j] | 15,000 | 136 |
| 1-hexenyl Me₂Si | 60800 | 180,000 | 136 |

[j]based on 30 minutes
[l]based on 45 minutes
[n]based on 10 minutes

Table 1 demonstrates that certain substituents at the 3-position on the indenyl result in a more active bridged indenyl/fluorenyl metallocene when the bridge is dimethyl methylene, i.e. isopropylidene. It also shows that the molecular weight was higher when the indenyl had a substituent in the 3 position.

A comparison of the control metallocene of Table 1 with the control of Table 2 demonstrates that the substitution of a phenyl group for one of the methyl groups of the bridge results in a more active catalyst. For many of the inventive metallocenes in Table 2 one does not see the dramatic improvement in activity over the control; however, the inventive metallocenes did produce polymers of much higher molecular weight. When the substituent on the 3 position of the indenyl was trimethyl silyl, 1-pentenyl, butyl, hexyl, benzyl, and 2-phenylethyl an improvement in activity was also noted.

Table 3 demonstrates that if the metallocene has a 1-methyl-1-(1-butenyl) methylene bridge a much more active catalyst is obtained if the indenyl has a trimethyl silyl group at the 3 position. Although the effect of a 1-butenyl group at the 3 position of the indenyl on the activity was not determined, the data also shows that such does result in a higher molecular weight polymer.

Table 4 demonstrates that substituents in the 3 position of the indenyl result in a much more active catalyst when the bridge is a dimethyl silyl bridge. The polymers also were generally slightly higher in molecular weight. Table 5 shows that the corresponding metallocenes in which one methyl substituent on the bridge was replaced with a phenyl group are even more active. Table 6 shows the results obtained using an indenyl/fluorenyl metallocene bridged by a diphenyl silyl group. Again those having a substituent at the 3 position on the indenyl were more active. Especially notable in Tables 4 and 6 is the activity obtained when the indenyl group is substituted in the 3 position by 1-pentenyl.

Table 7 should be compared with Table 8. The comparison shows that the inventive ethylene bridged metallocenes of Table 8, which have no branch on the bridge but which have a substituent in the 3 position of the indenyl are much more active than the catalysts of Table 7.

EXAMPLE 9

Self Immobilization of Catalyst

The metallocenes of the above examples were also evaluated to determine their ability to copolymerize with ethylene to form a prepolymerized particulate catalyst. The evaluations were conducted in Schlenk tubes. Approximately 10 mg of the metallocene was combined with about 10 ml of a 30 weight percent solution of methylaluminoxane in toluene and further diluted with 40 ml of toluene and exposed to an ethylene pressure of 0.4 to 0.6 bar. The insertion of the metallocene into the polymer chains was indicated by the characteristic coloration of the produced polymer precipitate.

The metallocenes having an omega olefin substituent were much more suitable for forming prepolymerized catalyst systems than those not containing such a substituent. The most effective were those having either a pentenyl or a hexenyl substituent at the 3 position on the indenyl.

That which is claimed is:

1. A bridged fluorenyl/indenyl containing metallocenes of the formula

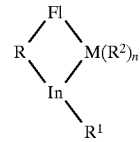

wherein R is a divalent organo radical connecting Fl and In, Fl is a 9-fluorenyl radical, In is an indenyl radical connected to R at the 1 position and to R¹ at the 3 position, wherein R and R¹ are the only substituents on In, wherein R¹ is selected from the group consisting of alkyl, aralkyl, alkenyl, alkylsilyl, alkenylsilyl, and alkoxyalkyl radicals having 1 to 20 carbon atoms, M is a metal selected from the group consisting of titanium, zirconium, hafnium, niobium, and tantalum, and each R² can be the same or different and is selected from hydrogen, halides, alkyl radicals containing 1 to 10 carbon atoms, aryl radicals having 6 to 12 carbon atoms, alkenyl radicals having 2 to 10 carbon atoms, arylalkyl radicals having 7 to 40 carbon atoms, arylalkenyl radicals having 8 to 40 carbon atoms, and alkylaryl radicals having 7 to 40 carbon atoms, n is a number to fill the remaining valences of M, further characterized by the fact that R¹ is not allyl or propenyl if R is dimethylsilyl.

2. A metallocene according to claim 1 wherein R is a divalent radical selected from the group consisting of dimethyl silyl, diphenyl silyl, phenyl methyl silyl, dimethyl methylene, 1-methyl-1-phenyl methylene, diphenyl methylene, alkenyl substituted ethylenes having 4 to 12 carbons, alkyl substituted ethylenes having 4 to 12 carbons, and 1,2-ethylene.

3. A metallocene according to claim 1 wherein $R^1$ is a radical selected from the group consisting of trialkyl silyls having 3 to 12 carbon atoms, 1-omega-alkenyl-1,1-dimethyl silyls in which the alkenyl group contains 2 to 10 carbon atoms, 1-omega-alkenyls having 2 to 10 carbon atoms, and alkyls having 1 to 10 carbon atoms.

4. A metallocene according to claim 3 wherein M is zirconium, n is 2, and $R^2$ is Cl.

5. A metallocene according to claim 4 wherein R is selected from the group consisting of dimethyl silyl and diphenyl silyl.

6. A metallocene according to claim 5 wherein $R^1$ is an omega-alkenyl radical having 4 to 6 carbon atoms.

7. A metallocene according to claim 6 wherein $R^1$ is 1-pentenyl.

8. A metallocene according to claim 7 wherein R is diphenyl silyl.

9. A metallocene according to claim 4 wherein R is selected from the group consisting of dimethyl methylene and phenyl methyl methylene.

10. A metallocene according to claim 9 wherein $R^1$ is selected from the group consisting of trimethyl silyl, omega-alkyenyls having 3 to 6 carbon atoms, and omega-alkenyl dimethyl silyls wherein the alkenyl group has 3 to 6 carbon atoms.

11. A metallocene according to claim wherein $R^1$ is 1-pentenyl.

12. A metallocene according to claim 11 wherein R is phenyl methyl methylene.

13. A metallocene according to claim 10 wherein R is dimethyl methylene.

14. A metallocene according to claim wherein $R^1$ is 5-hexenyl dimethyl silyl.

15. A metallocene according to claim 10 wherein R is phenyl methyl methylene.

16. A metallocene according to claim 4 wherein R is ethylidene.

17. A metallocene according to claim 17 wherein $R^1$ is an omega alkenyl having 4 to 6 carbon atoms.

18. A metallocene according to claim 1 wherein R is methyl omega-alkenyl methylene wherein the omega-alkenyl has 4 to 6 carbon atoms.

19. A metallocene according to claim 18 wherein R is methyl omega butenyl methylene.

20. A metallocene according to claim 19 wherein $R^1$ is an omega alkenyl.

21. A metallocene according to claim 20 wherein $R^1$ is 3-but-3-enyl.

22. A process for producing a polymer comprising contacting at least one olefin with a metallocene according to claim 1 under suitable polymerization conditions.

23. A process according to claim 22 wherein ethylene is polymerized and methylaluminoxane is used as a cocatalyst.

24. A process according to claim 23 wherein R is ethylidene.

25. A process according to claim 24 wherein $R^1$ is selected from the group consisting of omega alkenyl radicals having 4 to 6 carbon atoms.

26. A process according to claim 23 wherein R is methyl (omega alkenyl) methylene.

27. A process according to claim 23 wherein R is dimethyl methylene.

28. A process according to claim 27 wherein $R^1$ is 3-hex-5-enyldimethyl silyl.

29. A process according to claim 27 wherein $R^1$ is 3-pent-4-enyl.

30. A process according to claim 27 wherein $R^1$ is an omega alkenyl having 4 to 6 carbon atoms.

31. A process according to claim 30 wherein R is diphenyl silyl.

32. A process according to claim 30 wherein R is dimethyl silyl.

33. A process according to claim 23 wherein said polymerization is conducted using a catalyst system prepared by prepolymerizing said metallocene in the presence of aluminoxane and a particulate solid to obtain a particulate solid active as a polymerization catalyst.

34. A process for producing a bridged fluorenyl/indenyl ligand having a substituent a the 3-position of the indenyl comprising reacting lithium fluorenyl with a Benzofulyenes in diethylether to produce a bridged fluorenyl/indenyl ligand lithium salt and then reacting said ligand lithium salt with an organic halide selected from the group consisting of alkyl halides, alkenyl halides, and organosilyl halides.

35. A process according to claim 34 wherein the organic halide is selected from the group consisting of alkyl halides having 1 to 10 carbon atoms, 1-omega-alkenyl-1,1-dimethyl silyl halides in which the alkenyl group contains 2 to 10 carbon atoms, and 1-omega-alkenyl halides having 2 to 10 carbon atoms.

36. A process for preparing a bridged flourenyl/indenyl metallocene comprising carrying out the process of claim 34 and then reacting the resulting bridged fluorenyl/indenyl ligand with an alkyl lithium to produce the lithium salt and then reacting the lithium salt with a transition metal halide wherein the metal is selected from the group consisting of titanium, zirconium, hafnium, niobium, and tantalum.

\* \* \* \* \*

UNITED STATES PATENT AND TRADEMARK OFFICE
CERTIFICATE OF CORRECTION

PATENT NO. : 5,886,202
DATED : March 23, 1999
INVENTOR(S) : Michael Jung, Helmut G. Alt, M. Bruce Welch It is certified that error appears in the above-identified patent and that said Letters Patent is hereby corrected as shown below:

Claim 34, line 3, delete "Benzofulyenes", and insert therefor ---benzofulvene---.

Signed and Sealed this

Thirty-first Day of August, 1999

Attest:

Q. TODD DICKINSON

*Attesting Officer*         *Acting Commissioner of Patents and Trademarks*

UNITED STATES PATENT AND TRADEMARK OFFICE
CERTIFICATE OF CORRECTION

PATENT NO. : 5,886,202
DATED : March 23, 1999
INVENTOR(S) : Michael Jung, Helmut G. Alt, M. Bruce Welch It is certified that error appears in the above-identified patent and that said Letters Patent is hereby corrected as shown below:

Claim 34, line 2, after "substituent", please delete "a" and insert therefor ---at---.

Signed and Sealed this

Ninth Day of November, 1999

Attest:

Q. TODD DICKINSON

*Attesting Officer*                    *Acting Commissioner of Patents and Trademarks*